(12) United States Patent
Popp et al.

(10) Patent No.: US 7,692,788 B2
(45) Date of Patent: Apr. 6, 2010

(54) METHOD FOR QUICKLY DETERMINING QUALITIES/QUALITATIVE CHANGES IN ANY SYSTEM

(75) Inventors: Fritz-Albert Popp, Neuss (DE); Jürgen Mehlhase, Nideggen (DE); Zhongchen Yan, Neuss (DE)

(73) Assignee: Bipho Patentverwertung GmbH, Haan (DE)

( * ) Notice: Subject to any disclaimer, the term of this patent is extended or adjusted under 35 U.S.C. 154(b) by 317 days.

(21) Appl. No.: 10/558,471

(22) PCT Filed: Mar. 23, 2004

(86) PCT No.: PCT/DE2004/000590

§ 371 (c)(1), (2), (4) Date: Nov. 23, 2005

(87) PCT Pub. No.: WO2004/096971

PCT Pub. Date: Nov. 11, 2004

(65) Prior Publication Data

US 2007/0041010 A1     Feb. 22, 2007

(30) Foreign Application Priority Data

Apr. 25, 2003   (DE) ................................ 103 19 042

(51) Int. Cl.
    *G01N 21/63* (2006.01)
(52) U.S. Cl. .................................. 356/318; 356/417
(58) Field of Classification Search ................ 356/317, 356/318, 417
    See application file for complete search history.

(56) References Cited

U.S. PATENT DOCUMENTS 4,458,531 A     7/1984   Mehlhardt et al.

FOREIGN PATENT DOCUMENTS

| DE | 30 38 255 A1 | 5/1982 |
|----|----|----|
| DE | 30 40 855 A1 | 6/1982 |
| DE | 44 39 451 A1 | 5/1996 |
| DE | 4438863 A1 * | 5/1996 |
| DE | 10147701 A1 * | 4/2003 |
| EP | 0 430 150 A2 | 6/1991 |

OTHER PUBLICATIONS

Zalesskaya, Zhurnal Prikladnoi Spektroskopii, vol. 32, No. 1, Jan. 1980, pp. 34-40.*
Wrobel et al., Time-resolved delayed luminescence of chlorophyll a in anhydrous polymer systems, Spectrochimica Acta, Part A, vol. 52, 1996, pp. 97-105.*
Ho et al., Delayed luminescence from bovine Achilles' tendon and its dependence on collagen structure, Journal of Photochemistry and Photobiology B: Biology, vol. 66, 2002, pp. 165-170.*

* cited by examiner

*Primary Examiner*—F. L Evans
(74) *Attorney, Agent, or Firm*—Buchanan Ingersoll & Rooney PC

(57) ABSTRACT

The invention relates to a method for testing the slightest quality differences or quality features of any objects and agents interacting therewith based on measuring the percentage scatter of "ultraweak" photon emissions ("biophotons" in biological systems) and the delayed luminescence in a scatter chamber (darkroom). These scatter percentages can vary to such an extent as to enable the sufficiently sensitive registration of slightest quality differences (quality features).

4 Claims, No Drawings

METHOD FOR QUICKLY DETERMINING QUALITIES/QUALITATIVE CHANGES IN ANY SYSTEM

This disclosure is based upon German Application No. 103 19 042.2, filed Apr. 25, 2003, and International Application No. PCT/DE2004/000590, filed Mar, 23, 2004, the contents of which are incorporated herein by reference.

The invention relates to a method for quickly determining the quality/qualitative change in any system, in particular biological systems, e.g., eggs, by measuring the biophoton emission and delayed luminescence.

Known from EP-A-0430150 is that slight quality differences of biological systems can be quickly, reliably and non-invasively detected by means of biophoton emissions or delayed luminescence. These methods are based on measuring the intensity of weak light emissions from biological systems without and after external excitation, and utilize the differences in intensity or differences in characteristic decay functions of the delayed luminescence to draw conclusions as to the quality differences.

By contrast, the object of the invention is to establish a method for testing the quality of any system, e.g., solids, liquids, gaseous objects, entire foods like oranges, bananas or eggs.

This object is achieved with the features of the patent claim.

The invention is based on measuring the intensity of scattered light, e.g., on an egg, during and after illumination with a weak light source. It is based on the knowledge that even the simplest technical embodiments of the methods specified in EP-A-0430150 for testing the slightest quality changes of biological methods [sic] can be used to determine quality quickly and reliably enough, as documented here for eggs. All that must be done is to compare the intensity of incident light provided as a reference in a sufficiently accurate manner with the intensity changes caused by the presence of the sample-via light scatter. The method in EP-A-0430150 surprisingly also offers these advantages when registering the photons with the described suitably positioned and sufficiently sensitive detectors. In cases where quick checks are to be performed, this eliminates the need for complicated statistical analyses. Given a suitable technical realization, it can be performed in a time span of under one second per object, which can be tailored to existing requirements.

Filter systems including spectral filters and/or polarization filters and phase shifters may be used to filter the excitation light.

The invention utilizes specific knowledge from EP-A-0430150 in a special manner particularly advantageously, especially in a quick test, and logically enhances this knowledge.

The quickness of the method has special significance in a plurality of systems, including and especially eggs, or microbially attacked samples. There were previously no methods available that could satisfy the requirement for an extremely fast preliminary examination within a timeframe of seconds to minutes. For example, this holds true for microbial examinations, or also for tests on eggs. However, the shortest measuring periods are often required, e.g., for goods deliveries or when advantageously taking random samples for more thorough examinations.

The invention will now be described in greater detail below in an exemplary embodiment relating to a quick test for eggs.

A light source, e.g., a laser generator, relays monochromatic or white light into a measuring chamber (darkroom), in which the measuring object (e.g., an egg) is located. A shutter opens and closes access to the light channel (fiber optic). The scattered light is relayed via another sealable measuring channel to a photon counting system (e.g., photomultiplier). The light can here be introduced at a large distance from the scattered light channel (top figure) or at the smallest possible distance from the counting channel (bottom figure), depending on the shape of the object, and on whether absorption or scattering primarily yield the more reliable results on the object. Under certain conditions, the light intensity at the outlet channel becomes a reliable gauge for the quality (quality change) of the observed object.

TABLE 1

Example for the utilization of this method for eggs. 15 eggs are tested, which are known to deteriorate in quality from 1 to 15, wherein 1 is with certainty the best, and 15 with certainty the worst quality, wherein there are greater or smaller qualitative differences between the eggs.

| Scattered light value (in photons/s) | Quality (random units) |
|---|---|
| 400 | 1 |
| 380 | 2 |
| 376 | 3 |
| 310 | 4 |
| 308 | 5 |
| 309 | 6 |
| 310 | 7 |
| 278 | 8 |
| 267 | 9 |
| 252 | 10 |
| 250 | 11 |
| 252 | 12 |
| 223 | 13 |
| 212 | 14 |
| 178 | 15 |

Quality 1 (400 units) was achieved with an egg that was produced at a small farm by 20 optimally free roaming and fed hens under excellent climatic conditions and favorable summer weather. Quality 15 was obtained for an egg from battery farming. The values are also statistically buttressed, thereby ensuring sufficient reliability of the test in terms of individual assessment.

The invention claimed is:

1. A method for testing quality differences of microbially attacked systems by measuring photon emissions and luminescence, wherein samples are excited with laser light; scattering radiation of the objects is measured in darkened enclosures with or without interacting agents.

2. The method according to claim 1, wherein light guides are used, and wherein the input and output of the excitation light or light signals can be positioned as desired.

3. The method according to claim 1, wherein filter systems are used.

4. The method according to claim 3, wherein the filter systems include at least one of spectral filters, polarization filters, and phase shifters.

* * * * *